(12) United States Patent
Mozdzierz

(10) Patent No.: US 11,426,164 B2
(45) Date of Patent: Aug. 30, 2022

(54) SURGICAL BUTTRESS RETENTION SYSTEMS FOR SURGICAL STAPLING APPARATUS

(71) Applicant: Covidien LP, Mansfield, MA (US)

(72) Inventor: Patrick Mozdzierz, Glastonbury, CT (US)

(73) Assignee: Covidien LP, Mansfield, MA (US)

( * ) Notice: Subject to any disclaimer, the term of this patent is extended or adjusted under 35 U.S.C. 154(b) by 99 days.

(21) Appl. No.: 17/101,044

(22) Filed: Nov. 23, 2020

(65) Prior Publication Data
US 2021/0068833 A1  Mar. 11, 2021

Related U.S. Application Data

(63) Continuation of application No. 16/037,007, filed on Jul. 17, 2018, now Pat. No. 10,849,625.

(Continued)

(51) Int. Cl.
| | | |
|---|---|---|
| *A61B 17/072* | (2006.01) | |
| *A61B 17/068* | (2006.01) | |
| *A61B 17/00*  | (2006.01) | |

(52) U.S. Cl.
CPC .... *A61B 17/07292* (2013.01); *A61B 17/0682* (2013.01); *A61B 17/07207* (2013.01);
(Continued)

(58) Field of Classification Search
CPC .......... A61B 17/07292; A61B 17/0682; A61B 17/07207; A61B 2017/00004;
(Continued)

(56) References Cited

U.S. PATENT DOCUMENTS 3,054,406 A   9/1962 Usher
3,079,606 A   3/1963 Bobrov et al.
(Continued)

FOREIGN PATENT DOCUMENTS

CA   2282761 A1   9/1998
DE   1602563 U    3/1950
(Continued)

OTHER PUBLICATIONS

European Search Report corresponding to EP 06 00 4598, completed Jun. 22, 2006; (2 pp).
(Continued)

*Primary Examiner* — Dariush Seif
(74) *Attorney, Agent, or Firm* — Carter, DeLuca & Farrell LLP

(57) ABSTRACT

A surgical stapling apparatus includes a jaw assembly including an anvil assembly and a staple cartridge assembly, at least one which includes a surgical buttress retention system, and a surgical buttress releasably secured to a tissue facing surface of the anvil assembly or the staple cartridge assembly via the surgical buttress retention system. The surgical buttress retention system includes proximal guide slots defined in opposed sides of the anvil assembly or the staple cartridge assembly that have a generally U-shaped configuration that are mirror images of each other, a plug coupled to a distal portion of the anvil assembly or the staple cartridge assembly, and a retention member including a central portion extending across a proximal portion of the surgical buttress, second portions positioned within the proximal guide slots, third portions extending across a distal portion of the surgical buttress, and end portions coupled to the plug.

20 Claims, 4 Drawing Sheets

Related U.S. Application Data

(60) Provisional application No. 62/541,970, filed on Aug. 7, 2017.

(52) U.S. Cl.
CPC ............... *A61B 2017/00004* (2013.01); *A61B 2017/0053* (2013.01); *A61B 2017/00526* (2013.01); *A61B 2017/07257* (2013.01); *A61B 2017/07271* (2013.01); *A61B 2017/07278* (2013.01); *A61B 2017/07285* (2013.01)

(58) Field of Classification Search
CPC .. A61B 2017/00526; A61B 2017/0053; A61B 2017/07257; A61B 2017/07271; A61B 2017/07278; A61B 2017/07285
USPC .............. 227/175.1–182.1; 606/75, 219, 220
See application file for complete search history.

(56) References Cited

U.S. PATENT DOCUMENTS

| | | |
|---|---|---|
| 3,124,136 A | 3/1964 | Usher |
| 3,364,200 A | 1/1968 | Ashton et al. |
| 3,490,675 A | 1/1970 | Green et al. |
| 3,499,591 A | 3/1970 | Green |
| 3,797,494 A | 3/1974 | Zaffaroni |
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,112,496 A | 5/1992 | Dhawan et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,871,135 A | 2/1999 | Williamson, IV et al. |
| 5,874,500 A | 2/1999 | Rhee et al. |
| 5,895,412 A | 4/1999 | Tucker |
| 5,895,415 A | 4/1999 | Chow et al. |
| 5,902,312 A * | 5/1999 | Frater ............... A61B 17/07207 606/148 |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,394 A | 10/1999 | Robertson |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,142,933 A | 11/2000 | Longo et al. |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,270,530 B1 | 8/2001 | Eldridge et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,330,965 B1 | 12/2001 | Milliman et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,568,398 B2 | 5/2003 | Cohen |
| 6,590,095 B1 | 7/2003 | Schleicher et al. |
| 6,592,597 B2 | 7/2003 | Grant et al. |
| 6,605,294 B2 | 8/2003 | Sawhney |
| 6,610,006 B1 | 8/2003 | Amid et al. |
| 6,627,749 B1 | 9/2003 | Kumar |

(56) References Cited

U.S. PATENT DOCUMENTS

| | | | |
|---|---|---|---|
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,843,252 B2 | 1/2005 | Harrison et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |
| 7,009,034 B2 | 3/2006 | Pathak et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |
| 7,214,727 B2 | 5/2007 | Kwon et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,308,998 B2 | 12/2007 | Mastri et al. |
| 7,311,720 B2 | 12/2007 | Mueller et al. |
| 7,328,829 B2 | 2/2008 | Arad et al. |
| 7,334,717 B2 | 2/2008 | Rethy et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,464,849 B2 | 12/2008 | Shelton, IV et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,645,874 B2 | 1/2010 | Saferstein et al. |
| 7,649,089 B2 | 1/2010 | Kumar et al. |
| 7,655,288 B2 | 2/2010 | Bauman et al. |
| 7,662,409 B2 | 2/2010 | Masters |
| 7,662,801 B2 | 2/2010 | Kumar et al. |
| 7,665,646 B2 * | 2/2010 | Prommersberger ........................ A61B 17/07207 227/176.1 |
| 7,666,198 B2 | 2/2010 | Suyker et al. |
| 7,669,747 B2 | 3/2010 | Weisenburgh, II et al. |
| 7,673,782 B2 | 3/2010 | Hess et al. |
| 7,708,180 B2 | 5/2010 | Murray et al. |
| 7,709,631 B2 | 5/2010 | Harris et al. |
| 7,717,313 B2 | 5/2010 | Criscuolo et al. |
| 7,722,642 B2 | 5/2010 | Williamson, IV et al. |
| 7,735,703 B2 | 6/2010 | Morgan et al. |
| 7,744,627 B2 | 6/2010 | Orban, III et al. |
| 7,754,002 B2 | 7/2010 | Maase et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,819,896 B2 | 10/2010 | Racenet |
| 7,823,592 B2 | 11/2010 | Bettuchi et al. |
| 7,824,420 B2 | 11/2010 | Eldridge et al. |
| 7,845,533 B2 * | 12/2010 | Marczyk ........... A61B 17/07207 227/181.1 |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 * | 10/2011 | Stopek ............. A61B 17/07207 227/176.1 |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,091,756 B2 | 1/2012 | Viola |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,177,797 B2 | 5/2012 | Shimoji et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,790 B2 | 11/2012 | Bell et al. |
| 8,322,590 B2 | 12/2012 | Patel et al. |
| 8,348,126 B2 | 1/2013 | Olson et al. |
| 8,348,130 B2 | 1/2013 | Shah et al. |

(56) References Cited

U.S. PATENT DOCUMENTS

| | | |
|---|---|---|
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |
| 8,418,909 B2 | 4/2013 | Kostrzewski |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,470,360 B2 | 6/2013 | McKay |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,518,440 B2 | 8/2013 | Blaskovich et al. |
| 8,529,600 B2 | 9/2013 | Woodard, Jr. et al. |
| 8,540,128 B2 | 9/2013 | Shelton, IV et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | (Prommersberger) Stopek et al. |
| 8,617,132 B2 | 12/2013 | Golzarian et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,678,263 B2 | 3/2014 | Viola |
| 8,679,137 B2 | 3/2014 | Bauman et al. |
| 8,684,250 B2 | 4/2014 | Bettuchi et al. |
| 8,701,958 B2 | 4/2014 | Shelton, IV et al. |
| 8,721,703 B2 | 5/2014 | Fowler |
| 8,727,197 B2 | 5/2014 | Hess et al. |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,827,133 B2 | 9/2014 | Shelton, IV et al. |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,920,444 B2 | 12/2014 | Hiles et al. |
| 8,939,344 B2 | 1/2015 | Olson et al. |
| 8,956,390 B2 | 2/2015 | Shah et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | (Tarinelli) Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,328,111 B2 | 5/2016 | Zhou et al. |
| 9,345,479 B2 | 5/2016 | (Tarinelli) Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | (Prommersberger) Stopek et al. |
| 9,386,988 B2 | 7/2016 | Baxter, III et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,463,260 B2 | 10/2016 | Stopek |
| 9,486,215 B2 | 11/2016 | Olson et al. |
| 9,492,170 B2 | 11/2016 | Bear et al. |
| 9,504,470 B2 | 11/2016 | Milliman |
| 9,517,164 B2 | 12/2016 | Vitaris et al. |
| 9,572,576 B2 | 2/2017 | Hodgkinson et al. |
| 9,585,657 B2 | 3/2017 | Shelton, IV et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,636,850 B2 | 5/2017 | Stopek et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,687,262 B2 | 6/2017 | Rousseau et al. |
| 9,693,772 B2 | 7/2017 | Ingmanson et al. |
| 9,708,184 B2 | 7/2017 | Chan et al. |
| 9,770,245 B2 | 9/2017 | Swayze et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 9,918,713 B2 | 3/2018 | Zergiebel et al. |
| 9,931,116 B2 | 4/2018 | Racenet et al. |
| 10,022,125 B2 | 7/2018 | (Prommersberger) Stopek et al. |
| 10,849,625 B2 | 12/2020 | Mozdzierz |
| 2002/0091397 A1 | 7/2002 | Chen |
| 2002/0151911 A1 | 10/2002 | Gabbay |
| 2003/0065345 A1 | 4/2003 | Weadock |
| 2003/0078209 A1 | 4/2003 | Schmidt |
| 2003/0083676 A1 | 5/2003 | Wallace |
| 2003/0125676 A1 | 7/2003 | Swenson et al. |
| 2003/0181927 A1 | 9/2003 | Wallace |
| 2003/0208231 A1 | 11/2003 | Williamson et al. |
| 2004/0092912 A1 | 5/2004 | Jinno et al. |
| 2004/0107006 A1 | 6/2004 | Francis et al. |
| 2004/0131418 A1 | 7/2004 | Budde et al. |
| 2004/0254590 A1 | 12/2004 | Hoffman et al. |
| 2004/0260315 A1 | 12/2004 | Dell et al. |

(56) References Cited

U.S. PATENT DOCUMENTS

| | | |
|---|---|---|
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0149073 A1 | 7/2005 | Arani et al. |
| 2005/0283256 A1 | 12/2005 | Sommerich et al. |
| 2006/0004407 A1* | 1/2006 | Hiles ................ A61B 17/0644 606/215 |
| 2006/0008505 A1 | 1/2006 | Brandon |
| 2006/0025816 A1* | 2/2006 | Shelton, IV ...... A61B 17/07207 606/215 |
| 2006/0121266 A1 | 6/2006 | Fandel et al. |
| 2006/0173470 A1 | 8/2006 | Oray et al. |
| 2006/0190027 A1 | 8/2006 | Downey |
| 2007/0034669 A1 | 2/2007 | de la Torre et al. |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0216855 A1 | 9/2008 | Nasca |
| 2008/0220047 A1 | 9/2008 | Sawhney et al. |
| 2008/0290134 A1 | 11/2008 | Bettuchi et al. |
| 2009/0001121 A1 | 1/2009 | Hess et al. |
| 2009/0001130 A1 | 1/2009 | Hess et al. |
| 2009/0031842 A1 | 2/2009 | Kawai et al. |
| 2009/0134200 A1* | 5/2009 | Tarinelli ........... A61B 17/07207 227/176.1 |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1* | 8/2009 | Huitema .......... A61B 17/07207 227/176.1 |
| 2009/0218384 A1* | 9/2009 | Aranyi ............. A61B 17/07207 227/176.1 |
| 2009/0277944 A9 | 11/2009 | Dalessandro et al. |
| 2010/0016855 A1 | 1/2010 | Ramstein et al. |
| 2010/0016888 A1 | 1/2010 | Calabrese et al. |
| 2010/0087840 A1 | 4/2010 | Ebersole et al. |
| 2010/0147921 A1* | 6/2010 | Olson ................ A61B 17/105 227/175.1 |
| 2010/0147922 A1 | 6/2010 | Olson |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0243708 A1* | 9/2010 | Aranyi ............. A61B 17/07207 227/176.1 |
| 2010/0331859 A1 | 12/2010 | Omori |
| 2011/0034910 A1 | 2/2011 | Ross et al. |
| 2011/0087279 A1* | 4/2011 | Shah ................ A61B 17/07207 606/219 |
| 2011/0089220 A1 | 4/2011 | Ingmanson et al. |
| 2011/0125138 A1 | 5/2011 | Malinouskas et al. |
| 2011/0166673 A1 | 7/2011 | Patel et al. |
| 2011/0215132 A1* | 9/2011 | Aranyi ............. A61B 17/07207 227/176.1 |
| 2011/0270235 A1* | 11/2011 | Olson ............... A61B 17/07207 606/1 |
| 2011/0293690 A1 | 12/2011 | Griffin et al. |
| 2012/0080336 A1 | 4/2012 | Shelton, IV et al. |
| 2012/0145767 A1* | 6/2012 | Shah ................ A61B 17/07207 227/176.1 |
| 2012/0197272 A1 | 8/2012 | Oray et al. |
| 2012/0234900 A1* | 9/2012 | Swayze ........... A61B 17/07207 227/180.1 |
| 2012/0241491 A1 | 9/2012 | Aldridge et al. |
| 2012/0241493 A1 | 9/2012 | Baxter, III et al. |
| 2012/0253298 A1 | 10/2012 | Henderson et al. |
| 2012/0305626 A1 | 12/2012 | Stopek |
| 2013/0153636 A1 | 6/2013 | Shelton, IV et al. |
| 2013/0153641 A1* | 6/2013 | Shelton, IV ..... A61B 17/07292 227/180.1 |
| 2013/0256380 A1 | 10/2013 | Schmid et al. |
| 2014/0048580 A1* | 2/2014 | Merchant ......... A61B 17/07292 227/176.1 |
| 2014/0131418 A1* | 5/2014 | Kostrzewski .... A61B 17/07292 227/176.1 |
| 2014/0166721 A1* | 6/2014 | Stevenson ............ A61B 17/105 227/176.1 |
| 2014/0203061 A1* | 7/2014 | Hodgkinson .... A61B 17/07292 227/175.1 |
| 2014/0224686 A1* | 8/2014 | Aronhalt ......... A61B 17/07292 206/339 |
| 2014/0239047 A1 | 8/2014 | Hodgkinson et al. |
| 2015/0041347 A1 | 2/2015 | Hodgkinson |
| 2015/0122872 A1* | 5/2015 | Olson .............. A61B 17/07292 227/179.1 |
| 2015/0133995 A1 | 5/2015 | Shelton, IV et al. |
| 2015/0157320 A1 | 6/2015 | Zergiebel et al. |
| 2015/0157321 A1 | 6/2015 | Zergiebel et al. |
| 2015/0209045 A1 | 7/2015 | Hodgkinson et al. |
| 2015/0231409 A1* | 8/2015 | Racenet ........... A61B 17/07292 227/175.1 |
| 2015/0297236 A1* | 10/2015 | Harris ............... A61B 17/0644 227/176.1 |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0100834 A1 | 4/2016 | Viola et al. |
| 2016/0106430 A1 | 4/2016 | Carter et al. |
| 2016/0128694 A1* | 5/2016 | Baxter, III .......... A61B 17/068 227/176.1 |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0270793 A1 | 9/2016 | Carter et al. |
| 2016/0278776 A1* | 9/2016 | Shelton, IV ......... A61B 17/068 |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0055981 A1* | 3/2017 | Vendely .............. A61B 17/068 |
| 2017/0119390 A1* | 5/2017 | Schellin ............... A61B 17/32 |
| 2017/0150967 A1 | 6/2017 | Hodgkinson et al. |
| 2017/0172575 A1* | 6/2017 | Hodgkinson ....... A61B 17/1155 |
| 2017/0231629 A1 | 8/2017 | Stopek et al. |
| 2017/0238931 A1 | 8/2017 | Prescott et al. |
| 2017/0281328 A1 | 10/2017 | Hodgkinson et al. |
| 2017/0296188 A1 | 10/2017 | Ingmanson et al. |
| 2017/0354415 A1* | 12/2017 | Casasanta, Jr. ...... A61B 17/068 |
| 2018/0125491 A1* | 5/2018 | Aranyi ............. A61B 17/07207 |
| 2018/0140301 A1 | 5/2018 | Milliman |
| 2018/0168654 A1 | 6/2018 | Hodgkinson et al. |
| 2018/0214147 A1 | 8/2018 | Merchant et al. |
| 2018/0250000 A1* | 9/2018 | Hodgkinson ........ A61N 5/1007 |
| 2018/0256164 A1* | 9/2018 | Aranyi ............... A61B 5/6858 |
| 2019/0038285 A1* | 2/2019 | Mozdzierz ....... A61B 17/07292 |
| 2019/0343521 A1* | 11/2019 | Williams ........ A61B 17/07292 |
| 2021/0290230 A1* | 9/2021 | Fernandes ....... A61B 17/07207 |

FOREIGN PATENT DOCUMENTS

| | | |
|---|---|---|
| DE | 19924311 A1 | 11/2000 |
| EP | 0327022 A2 | 8/1989 |
| EP | 0594148 A1 | 4/1994 |
| EP | 2491867 A1 | 8/2012 |
| JP | 2000166933 A | 6/2000 |
| JP | 2002202213 A | 7/2002 |
| JP | 2007124166 A | 5/2007 |

(56) References Cited

FOREIGN PATENT DOCUMENTS

| JP | 2010214132 A | 9/2010 |
|---|---|---|
| WO | 9005489 A1 | 5/1990 |
| WO | 95/16221 A1 | 6/1995 |
| WO | 98/38923 A1 | 9/1998 |
| WO | 9926826 A2 | 6/1999 |
| WO | 0010456 A1 | 3/2000 |
| WO | 0016684 A1 | 3/2000 |
| WO | 2010075298 A2 | 7/2010 |

OTHER PUBLICATIONS

European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008; (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541.4, completed Apr. 23, 2012 and dated May 3, 2012; (10 pp).
European Search Report corresponding to EP 12 16 5609.4, completed Jul. 5, 2012 and dated Jul. 13, 2012; (8 pp).
European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated May 27, 2013; (8 pp).
Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 2013; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).
Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 4, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
Extended European Search Report corresponding to EP 13 19 4995.0, completed Jun. 5, 2014 and dated Jun. 16, 2014; (5 pp).
Extended European Search Report corresponding to EP 14 15 7195.0, completed Jun. 5, 2014 and dated Jun. 18, 2014; (9 pp).
Extended European Search Report corresponding to EP 14 15 6342.9, completed Jul. 22, 2014 and dated Jul. 29, 2014; (8 pp).
European Office Action corresponding to EP 12 19 8776.2 dated Jan. 19, 2016.
Extended European Search Report corresponding to EP 15 17 4146.9 dated Jan. 20, 2016.
Chinese First Office Action corresponding to CN 201310353628.5 dated Jan. 25, 2016.
Extended European Search Report corresponding to EP 12 19 6912.5 dated Feb. 1, 2016.
Japanese Office Action corresponding to JP 2012-098903 dated Feb. 22, 2016.
Extended European Search Report corresponding to EP 12 19 8753.1 dated Feb. 24, 2016.
Chinese First Office Action corresponding to CN 201410449019.4 dated Mar. 30, 2016.
Extended European Search Report corresponding to EP 16 15 0232.3 dated Apr. 12, 2016.
European Office Action corresponding to EP 11 18 3256.4 dated Apr. 20, 2016.
Australian Examination Report No. 1 corresponding to AU 2012244169 dated May 10, 2016.
European Office Action corresponding to EP 10 25 0715.9 dated May 12, 2016.
Chinese First Office Action corresponding to CN 201410778512.0 dated May 13, 2016.
Australian Examination Report No. 1 corresponding to AU 2012227358 dated May 16, 2016.
Japanese Office Action corresponding to JP 2012-040188 dated May 17, 2016.

(56) References Cited

OTHER PUBLICATIONS

Australian Examination Report No. 1 corresponding to AU 2012244380 dated May 20, 2016.
Australian Examination Report No. 1 corresponding to AU 2014227480 dated May 21, 2016.
Australian Examination Report No. 1 corresponding to AU 2012254977 dated May 30, 2016.
Japanese Office Action corresponding to JP 2013-147701 dated Mar. 21, 2017.
Australian Examination Report No. 1 corresponding to AU 2013206804 dated Mar. 21, 2017.
Australian Examination Report No. 1 corresponding to AU 2013211499 dated May 4, 2017.
Australian Examination Report No. 1 corresponding to AU 2014201008 dated May 23, 2017.
European Office Action corresponding to EP 15 17 4146.9 dated May 15, 2017.
Japanese Office Action corresponding to JP 2013-154561 dated May 23, 2017.
European Office Action corresponding to EP 12 19 4784.0 dated May 29, 2017.
Japanese Office Action corresponding to JP 2013-169083 dated May 31, 2017.
Australian Examination Report No. 1 corresponding to AU 2013213767 dated Jun. 29, 2017.
Australian Examination Report No. 2 corresponding to AU 2012261752 dated Jul. 7, 2017.
Australian Examination Report No. 1 corresponding to AU 2013266989 dated Jul. 10, 2017.
Extended European Search Report corresponding to EP 14 15 3609.4 dated Jul. 14, 2017.
Australian Examination Report No. 1 corresponding to AU 2013234418 dated Jul. 14, 2017.
Extended European Search Report corresponding to EP 14 15 3610.2 dated Jul. 17, 2017.
Australian Examination Report No. 1 corresponding to AU 2014200109 dated Jul. 20, 2017.
Australian Examination Report No. 1 corresponding to AU 2014200074 dated Jul. 20, 2017.
Japanese Office Action corresponding to JP 2013-250857 dated Aug. 17, 2017.
Japanese Office Action corresponding to JP 2013-229471 dated Aug. 17, 2017.
Extended European Search Report corresponding to EP 14 16 9739.1, completed Aug. 19, 2014 and dated Aug. 29, 2014; (7 pp).
Extended European Search Report corresponding to EP 14 15 7997.9, completed Sep. 9, 2014 and dated Sep. 17, 2014; (8 pp).
Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).
Extended European Search Report corresponding to EP 13 15 4571.7, completed Oct. 10, 2014 and dated Oct. 20, 2014; (8 pp).
Extended European Search Report corresponding to EP 14 18 1125.7, completed Oct. 16, 2014 and dated Oct. 24, 2014; (7 pp).
Extended European Search Report corresponding to EP 14 18 1127.3, completed Oct. 16, 2014 and dated Nov. 10, 2014; (8 pp).
Extended European Search Report corresponding to EP 14 19 0419.3, completed Mar. 24, 2015 and dated Mar. 30, 2015; (6 pp).
European Office Action corresponding to EP 12 198 776.2 dated Apr. 7, 2015.
European Office Action corresponding to EP 13 156 297.7 dated Apr. 10, 2015.
Australian Examination Report No. 1 corresponding to AU 2011250822 dated May 18, 2015.
European Office Action corresponding to EP 12 186 175.1 dated Jun. 1, 2015.
Chinese Office Action corresponding to CN 201010517292.8 dated Jun. 2, 2015.
Extended European Search Report corresponding to EP 14 17 4814.5 dated Jun. 9, 2015.
Australian Examination Report No. 1 corresponding to AU 2014200584 dated Jun. 15, 2015.
European Office Action corresponding to EP 13 180 881.8 dated Jun. 19, 2015.
European Office Action corresponding to EP 14 157 195.0 dated Jul. 2, 2015.
Extended European Search Report corresponding to EP 12 19 6902.6 dated Aug. 6, 2015.
Extended European Search Report corresponding to EP 14 15 2060.1 dated Aug. 14, 2015.
Chinese Office Action corresponding to CN 201210129787.2 dated Aug. 24, 2015.
Canadian Office Action corresponding to CA 2,665,206 dated Nov. 19, 2013.
Chinese Notification of Reexamination corresponding to CN 201010517292.8 dated Jun. 2, 2015.
Japanese Office Action corresponding to JP 2014-216989 dated Sep. 11, 2015.
Canadian First Office Action corresponding to CA 2,686,105 dated Sep. 17, 2015.
Japanese Office Action corresponding to JP 2012-040188 dated Oct. 21, 2015.
European Communication corresponding to EP 13 17 6895.4 dated Nov. 5, 2015.
Chinese First Office Action corresponding to CN 201210544552 dated Nov. 23, 2015.
Chinese First Office Action corresponding to CN 201210545228 dated Nov. 30, 2015.
Extended European Search Report corresponding to EP 15 18 0491.1 dated Dec. 9, 2015.
Extended European Search Report corresponding to EP 15 18 3819.0 dated Dec. 11, 2015.
Canadian Office Action corresponding to CA 2,697,819 dated Jan. 6, 2016.
Canadian Office Action corresponding to CA 2,696,419 dated Jan. 14, 2016.
Australian Examination Report No. 1 corresponding to AU 2014200793 dated Sep. 2, 2017.
Extended European Search Report corresponding to EP 17 17 8528.0 dated Oct. 13, 2017.
Australian Examination Report No. 1 corresponding to AU 2013234420 dated Oct. 24, 2017.
Japanese Office Action corresponding to JP 2013-175379 dated Oct. 20, 2017.
Japanese Office Action corresponding to JP 2013-147701 dated Oct. 27, 2017.
Extended European Search Report corresponding to EP 17 17 5656.2 dated Nov. 7, 2017.
Japanese Office Action corresponding to JP 2014-009738 dated Nov. 14, 2017.
European Office Action corresponding to EP 13 17 3986.4 dated Nov. 29, 2017.
Japanese Office Action corresponding to JP 2017-075975 dated Dec. 4, 2017.
European Office Action corresponding to EP 13 19 7958.5 dated Dec. 11, 2017.
Chinese First Office Action corresponding to Patent Application CN 201410588811.8 dated Dec. 5, 2017.
European Office Action corresponding to Patent Application EP 16 16 6367.9 dated Dec. 11, 2017.
Chinese First Office Action corresponding to Patent Application CN 201610279682.3 dated Jan. 10, 2018.
Japanese Office Action corresponding to Patent Application JP 2013-154561 dated Jan. 15, 2018.
Australian Examination Report No. 1 corresponding to Patent Application AU 2017225037 dated Jan. 23, 2018.
Japanese Office Action corresponding to Patent Application JP 2013-229471 dated May 1, 2018.
Canadian Office Action corresponding to Patent Application CA 2,790,743 dated May 14, 2018.

(56) References Cited

OTHER PUBLICATIONS

European Office Action corresponding to Patent Application EP 14 15 7195.0 dated Jun. 12, 2018.
European Office Action corresponding to EP 14 17 2681.0 dated May 13, 2016.
Extended European Search Report corresponding to EP 16 15 3647.9 dated Jun. 3, 2016.
Chinese Office Action corresponding to CN 201210545228 dated Jun. 29, 2016.
Japanese Office Action corresponding to JP 2012-250058 dated Jun. 29, 2016.
European Office Action corresponding to EP 14 15 7997.9 dated Jun. 29, 2016.
Canadian Office Action corresponding to CA 2,712,617 dated Jun. 30, 2016.
Chinese First Office Action corresponding to CN 2013103036903 dated Jun. 30, 2016.
Australian Patent Examination Report No. 1 corresponding to AU 2012250278 dated Jul. 10, 2016.
Australian Patent Examination Report No. 1 corresponding to AU 2012244382 dated Jul. 10, 2016.
Japanese Office Action corresponding to 2012-255242 dated Jul. 26, 2016.
Japanese Office Action corresponding to JP 2012-268668 dated Jul. 27, 2016.
European Office Action corresponding to EP 14 15 2060.1 dated Aug. 4, 2016.
European Office Action corresponding to EP 12 16 5609.4 dated Aug. 5, 2016.
European Office Action corresponding to EP 15 15 2392.5 dated Aug. 8, 2016.
Japanese Office Action corresponding to JP 2013-003624 dated Aug. 25, 2016.
Australian Patent Examination Report No. 1 corresponding to AU 2012261752 dated Sep. 6, 2016.
Japanese Office Action corresponding to JP 2014-252703 dated Sep. 26, 2016.
European Office Action corresponding to EP 12 19 8776.2 dated Sep. 12, 2016.
Japanese Office Action corresponding to JP 2013-000321 dated Sep. 13, 2016.
Chinese Second Office Action corresponding to CN 201310353628.5 dated Sep. 26, 2016.
European Office Action corresponding to EP 12 15 2541.4 dated Sep. 27, 2016.
Australian Patent Examination Report No. 1 corresponding to AU 2012268923 dated Sep. 28, 2016.
Chinese First Office Action corresponding to CN 2013107068710 dated Dec. 16, 2016.
Chinese First Office Action corresponding to CN 201310646606.8 dated Dec. 23, 2016.
Japanese Office Action corresponding to JP 2013-000321 dated Jan. 4, 2017.
Extended European Search Report corresponding to EP 16 16 6367.9 dated Jan. 16, 2017.
Australian Examination Report No. 1 corresponding to AU 2013206777 dated Feb. 1, 2017.
Chinese Second Office Action corresponding to CN 2013103036903 dated Feb. 23, 2017.
Japanese Office Action corresponding to JP 2013-175379 dated Mar. 1, 2017.
Chinese First Office Action corresponding to CN 201410028462.4 dated Mar. 2, 2017.
Chinese First Office Action corresponding to CN 201410084070 dated Mar. 13, 2017.
Extended European Search Report corresponding to EP 16 19 6549.6 dated Mar. 17, 2017.

\* cited by examiner

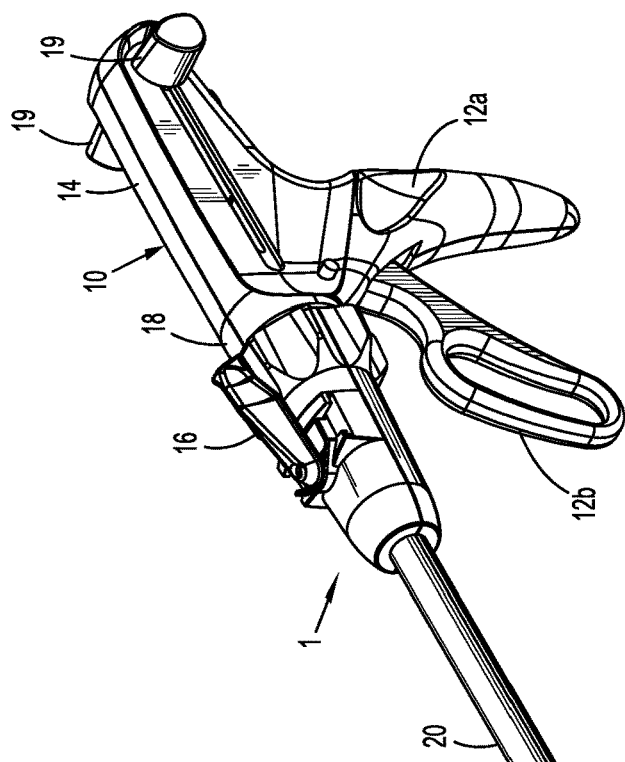
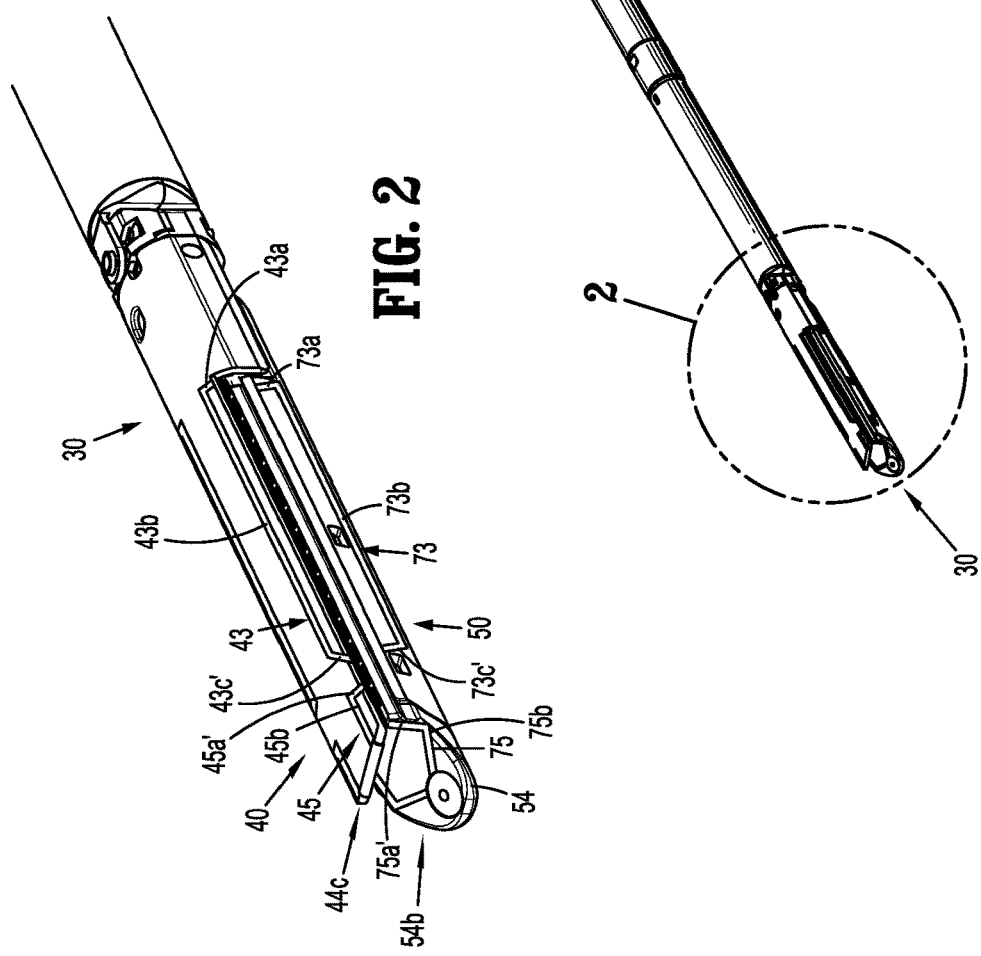

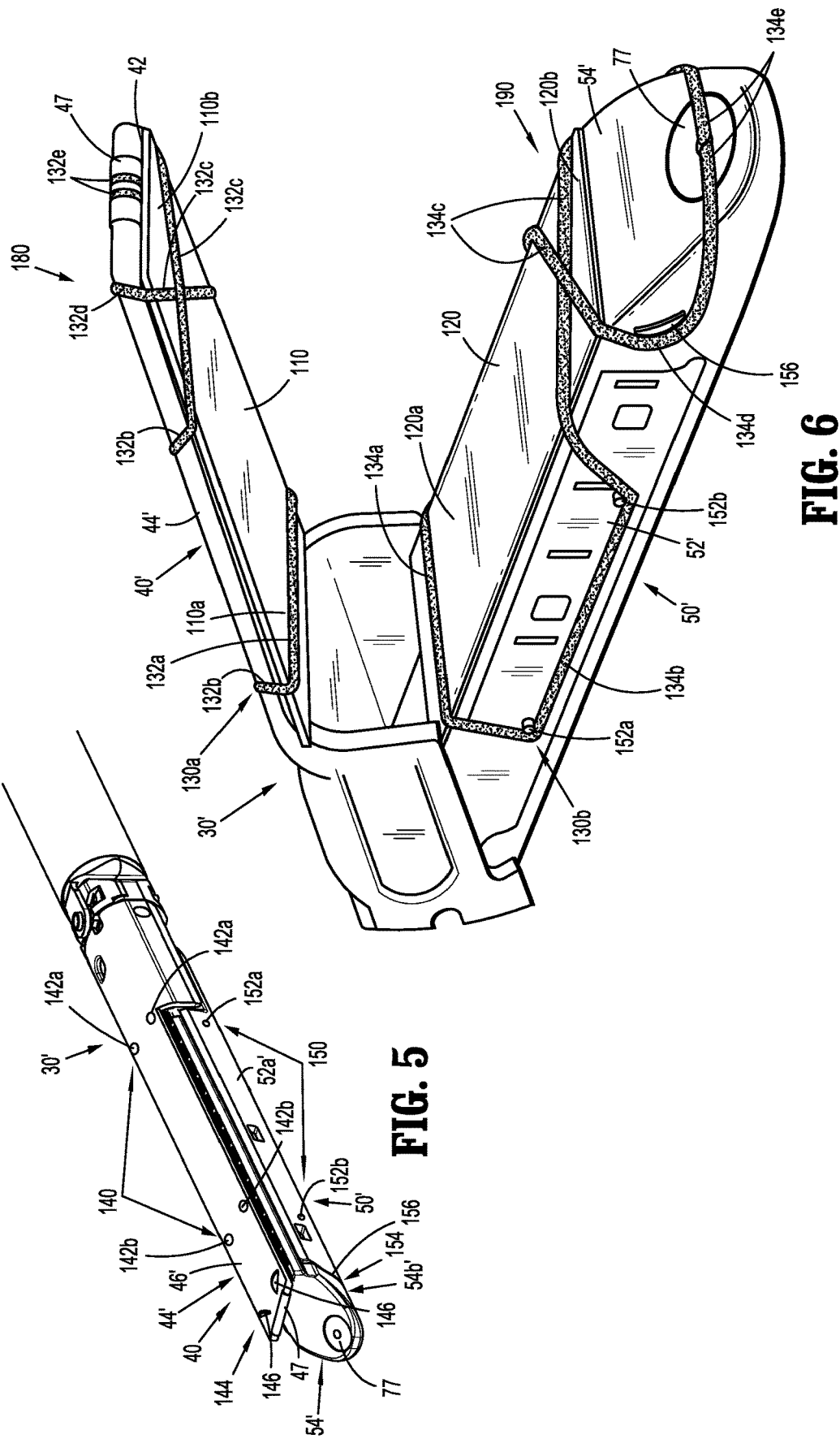

SURGICAL BUTTRESS RETENTION SYSTEMS FOR SURGICAL STAPLING APPARATUS

CROSS-REFERENCE TO RELATED APPLICATIONS

This application is a continuation of U.S. patent application Ser. No. 16/037,007, filed Jul. 17, 2018 (now U.S. Pat. No. 10,849,625), which claims the benefit of and priority to U.S. Provisional Patent Application No. 62/541,970, filed Aug. 7, 2017, the entire disclosure of each of which is incorporated by reference herein.

BACKGROUND

1. Technical Field

The present disclosure relates to surgical buttresses for use with surgical stapling apparatus, and more particularly, to surgical buttress retention systems for releasably securing surgical buttresses to the surgical stapling apparatus.

2. Background of Related Art

Surgical stapling apparatus are employed by surgeons to sequentially or simultaneously apply one or more rows of fasteners, e.g., staples or two-part fasteners, to body tissue for the purpose of joining segments of body tissue together. Such apparatus generally include a pair of jaws or finger-like structures between which the body tissue to be joined is placed. When the surgical stapling apparatus is actuated, or "fired", longitudinally moving firing bars contact staple drive members in one of the jaws. The staple drive members push the surgical staples through the body tissue and into an anvil in the opposite jaw which forms the staples. If body tissue is to be removed or separated, a knife blade can be provided in the jaws of the apparatus to cut the body tissue between the lines of staples.

Surgical supports, e.g., meshes or buttress materials, may be used in combination with surgical stapling apparatus to bridge, repair, and/or reinforce tissue defects within a patient such as those occurring, for example, in the abdominal wall, chest wall, diaphragm, or musculo-aponeurotic areas of the body. The buttress material reinforces the staple line as well as covers the juncture of the tissues to reduce leakage prior to healing.

Some current surgical stapling apparatus incorporate one or more sutures that tie down proximal and distal portions of a buttress material onto a jaw of the surgical stapling apparatus. The proximal suture tie down is released when the knife blade is passed down the staple line, bisecting the suture disposed over the proximal portion of the buttress material. The distal suture tie down is released when the knife blade bisects the suture disposed over the distal portion of the buttress material or actuates a distal cutting mechanism to sever the suture.

Such designs, however, require a full firing stroke to free the buttress material from the surgical stapling apparatus. Accordingly, if actuation of the surgical stapling apparatus is terminated prior to a full firing stroke, the distal suture tie down is not severed and the buttress material is not released from the surgical stapling apparatus. When this occurs, the buttress material is stapled to the tissue and is still distally attached to the surgical stapling apparatus, requiring surgical intervention (e.g., scissors) to sever the distal suture tie down to free the buttress material from the surgical stapling apparatus.

SUMMARY

The present disclosure is directed to surgical buttress retention systems for retaining and/or tensioning a surgical buttress to a jaw of a surgical stapling apparatus and that require only a single proximal cut to release the surgical buttress from the jaw. This configuration releases the surgical buttress in the event of partial firing of the surgical stapling apparatus without requiring additional surgical intervention for releasing the surgical buttress from the surgical stapling apparatus.

According to an aspect of the present disclosure, a surgical stapling apparatus includes a jaw assembly including an anvil assembly and a staple cartridge assembly, at least one of which includes a surgical buttress retention system, and a surgical buttress releasably secured to a tissue facing surface of the anvil assembly or the staple cartridge assembly via the surgical buttress retention system. The surgical buttress retention system includes proximal guide slots defined in opposed sides of the anvil assembly or the staple cartridge assembly that have a generally U-shaped configuration that are mirror images of each other, a plug coupled to a distal portion of the anvil assembly or the staple cartridge assembly, and a retention member including a central portion extending across a proximal portion of the surgical buttress, second portions positioned within the proximal guide slots, third portions extending across a distal portion of the surgical buttress, and end portions coupled to the plug.

The proximal guide slots may have a central segment extending longitudinally along the anvil assembly or the staple cartridge assembly, and first and second leg segments each extending at an angle with respect to the central segment. In embodiments, the first leg segment is disposed at about a 90° angle with respect to the central segment. In some embodiments, the second leg segment is disposed at about a 90° angle with respect to the central segment and, in certain embodiments, the second leg segment is disposed at about a 135° angle with respect to the central segment.

The plug may be rotatable relative to the anvil assembly or the staple cartridge assembly to tension the retention member on the anvil assembly or the staple cartridge assembly. In embodiments, the plug includes an aperture defined therethrough that is configured to retain the end portions of the retention member.

The surgical buttress retention system may further include distal guide slots defined in opposed sides of the anvil assembly or the staple cartridge assembly in longitudinally spaced relation relative to the proximal guide slots. The distal guide slots may have a generally L-shaped configuration that are mirror images of each other, and fourth portions of the retention member may be positioned within the distal guide slots. In embodiments, the distal guide slots each have first and second leg segments disposed at an angle with respect to each other. In some embodiments, the first leg segment is disposed at about a 90° angle with respect to the second leg segment, and the second leg segment extends longitudinally along the anvil assembly or the staple cartridge assembly. In certain embodiments, the first leg segment is disposed at about a 135° angle with respect to the second leg segment, and the second leg segment extends longitudinally along the anvil assembly or the staple cartridge assembly. The third portions of the retention member may cross each other over the distal portion of the surgical buttress.

In embodiments, the surgical buttress retention system secures the surgical buttress to the anvil assembly. The anvil assembly includes an anvil plate and an anvil cover secured over the anvil plate, and the proximal and distal guide slots are recessed in an outer surface of the anvil cover. In some embodiments, the plug is press fit into an aperture defined in a distal end of the anvil cover.

In embodiments, the surgical buttress retention system secures the surgical buttress to the staple cartridge assembly. The staple cartridge assembly includes a staple cartridge disposed within a cartridge carrier. The proximal guide slots are recessed in side surfaces of the cartridge carrier and/or the distal guide slots are recessed in an outer surface of the staple cartridge. In some embodiments, the plug is press fit into an aperture defined in a distal portion of the staple cartridge.

According to another aspect of the present disclosure, a method of loading a surgical buttress onto a jaw assembly of a surgical stapling apparatus includes: placing a surgical buttress on a tissue facing surface of an anvil assembly or a staple cartridge assembly; positioning a central portion of a retaining member over a proximal portion of the surgical buttress; threading second portions of the retaining member through proximal guide slots disposed on opposed sides of the anvil assembly or the staple cartridge assembly; crossing third portions of the retaining member over a distal portion of the surgical buttress; and coupling end portions of the retaining member to a plug engaged with a distal portion of the anvil assembly or the staple cartridge assembly.

In embodiments, the method further includes threading fourth portions of the retaining member through distal guide slots disposed on opposed sides of the anvil assembly or the staple cartridge assembly in longitudinally spaced relation relative to the proximal guide slots. In some embodiments, the method further includes rotating the plug to tension the retaining member on the anvil assembly or the staple cartridge assembly.

Other aspects, features, and advantages will be apparent from the description, drawings, and the claims.

BRIEF DESCRIPTION OF THE DRAWINGS

Various aspects of the present disclosure are described herein below with reference to the drawings, which are incorporated in and constitute a part of this specification, wherein:

FIG. 1 is a side, perspective view of a surgical stapling apparatus in accordance with an embodiment of the present disclosure;

FIG. 2 is an enlarged, perspective view of the area of detail identified in FIG. 1, illustrating anvil and staple cartridge assemblies of a jaw assembly of the surgical stapling apparatus in accordance with an embodiment of the present disclosure;

FIG. 5 is a side, perspective view of a jaw assembly for use with the surgical stapling apparatus of FIG. 1, in accordance with another embodiment of the present disclosure; and FIG. 6 is an end, perspective view of the jaw assembly of FIG. 5, including surgical buttresses releasably secured to anvil and staple cartridge assemblies of the jaw assembly via retention members in accordance with another embodiment of the present disclosure.

DETAILED DESCRIPTION OF THE EMBODIMENTS

Figure 3:
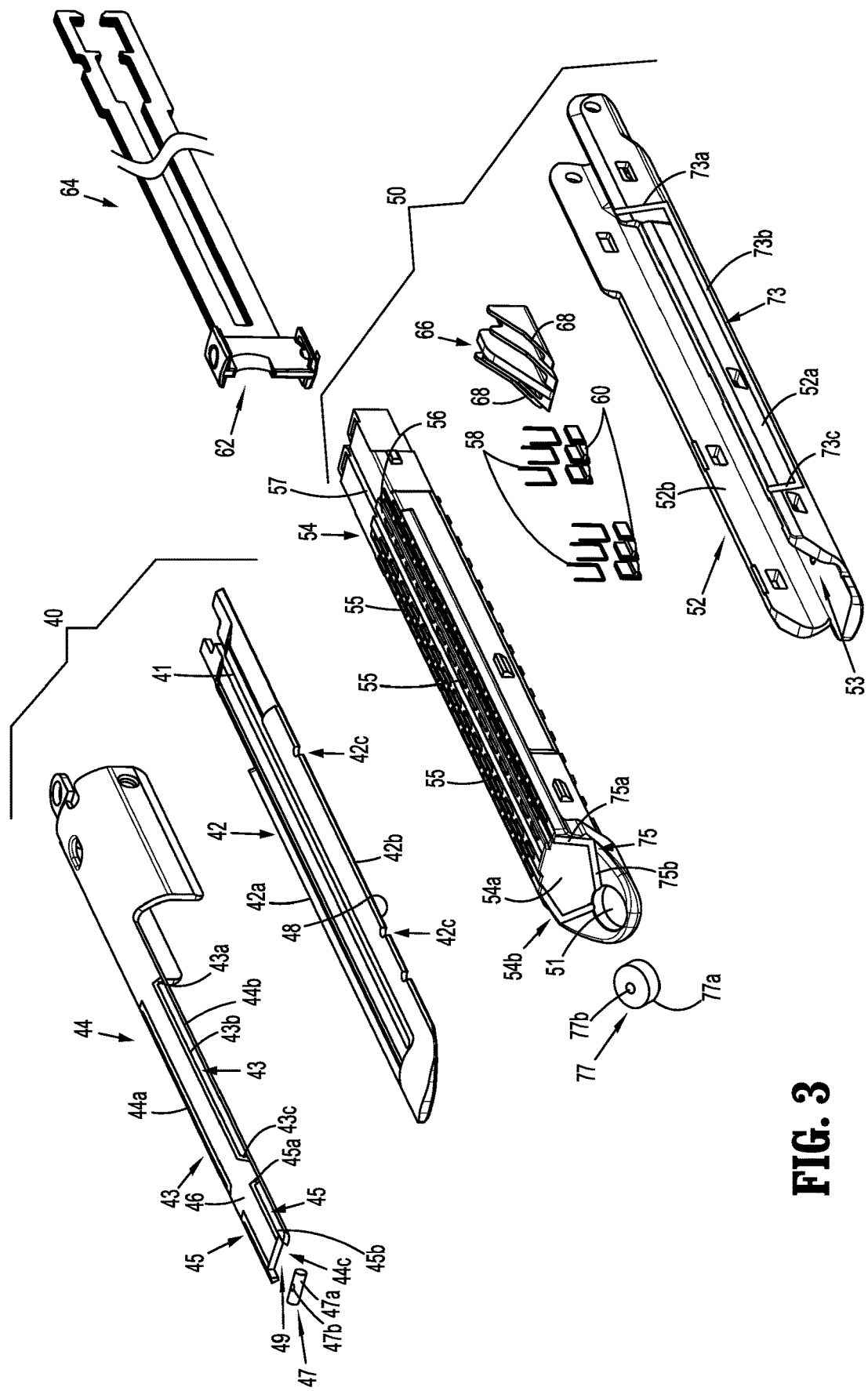
FIG. 3 is an exploded, perspective view of anvil and staple cartridge assemblies of a jaw assembly for use with the surgical stapling apparatus of FIG. 1 in accordance with another embodiment of the present disclosure.

Various exemplary embodiments of the present disclosure are discussed herein below in terms of surgical buttress retention systems for releasably securing surgical buttresses to a surgical stapling apparatus. The surgical buttresses described herein may be used in sealing a wound by approximating the edges of wound tissue between a staple cartridge assembly and an anvil assembly of a surgical stapling apparatus which includes at least one surgical buttress. The surgical buttress is releasably attached to the surgical stapling apparatus by a surgical buttress retention system that is configured to secure both proximal and distal portions of the surgical buttress to the surgical stapling apparatus and to release both the proximal and distal portions of the surgical buttress from the surgical stapling apparatus during cutting of only the proximal portion of the surgical buttress during firing of the surgical stapling apparatus.

Embodiments of the presently disclosed surgical buttress retention systems will now be described in detail with reference to the drawing figures wherein like reference numerals identify similar or identical elements. Throughout this description, the term "proximal" refers to a portion of a structure, or component thereof, that is closer to a user, and the term "distal" refers to a portion of the structure, or component thereof, that is farther from the user. Directional reference terms, such as "top," "bottom," "side," and the like, are intended to ease description of the embodiments and are not intended to have any limiting effect on the ultimate orientations of a structure or any parts thereof.

Referring now to FIGS. 1 and 2, an exemplary surgical stapling apparatus or surgical stapler 1 is shown for use in stapling tissue and applying one or more buttress materials or surgical buttresses to the tissue. The surgical stapling apparatus 1 generally includes a handle assembly 10, an elongate tubular body portion 20 extending distally from the handle assembly 10, and an end effector or jaw assembly 30 extending distally from the elongate tubular body portion 20. The jaw assembly 30 includes an anvil assembly 40 and a staple cartridge assembly 50. The jaw assembly 30 may be permanently affixed to the elongate tubular body portion 20 or may be detachable with respect to the elongate tubular body portion 20 and thus, replaceable with a new jaw assembly 30. The anvil assembly 40 and/or the staple cartridge assembly 50 is pivotable with respect to the elongate tubular body portion 20 such that the anvil and staple cartridge assemblies 40, 50 are movable between an open position in which the anvil and staple cartridge assemblies 40, 50 are spaced apart with respect to each other and a closed position in which the anvil and staple cartridge assemblies 40, 50 are substantially adjacent each other.

The handle assembly 10 includes a stationary handle member 12a, a movable handle member 12b, and a barrel portion 14. An articulation lever 16 is mounted on the forward end of the barrel portion 14 to facilitate articulation of the jaw assembly 30. A rotatable member 18 is also mounted on the forward end of the barrel portion 14, adjacent the articulation lever 16. Rotation of the rotatable member 18 relative to the barrel portion 14 rotates the elongate tubular body portion 20 and the jaw assembly 30 relative to the handle assembly 10 so as to properly orient the anvil and staple cartridge assemblies 40, 50 relative to tissue to be stapled. A pair of knobs 19 is movably positionable along the barrel portion 14. The pair of knobs 19 is advanced distally to approximate or close the anvil and staple cartridge assemblies 40, 50, relative to each other, and retracted proximally to unapproximate or open the anvil and staple cartridge assemblies 40, 50, with respect to each other. Actuation of the movable handle member 12b applies lines of staples 58 (FIG. 3) to tissue captured between the anvil and staple cartridge assemblies 40, 50.

As seen in FIG. 3, the anvil assembly 40 includes an anvil plate 42 having a central longitudinal slot 41 formed therein, and a cover plate 44 secured over the anvil plate 42 such that the cover plate 44 defines a top or outwardly facing surface 46 of the anvil assembly 40. The anvil plate 42 may include a plurality of staple forming pockets/cavities (not shown) defined in an inward or tissue facing surface 48 thereof.

The staple cartridge assembly 50 includes a cartridge carrier 52 defining an elongated support channel 53 configured and dimensioned to selectively receive a staple cartridge 54 therein. The staple cartridge 54 is removable and replaceable in the cartridge carrier 52 of the staple cartridge assembly 50. The staple cartridge 54 includes an inward or tissue facing surface 56 defining staple pockets or retention slots 55 formed therein for receiving a plurality of fasteners or staples 58 and staple pushers 60. A central longitudinal slot 57 is formed in and extends along a substantial length of the staple cartridge 54 to facilitate passage of a knife blade 62 of a drive bar 64 therethrough. During operation of the surgical stapler 1, an actuation sled 66 translates through the staple cartridge 54 to advance cam wedges 68 of the actuation sled 66 into sequential contact with the staple pushers 60, to cause the staple pushers 60 to translate vertically within the staple pockets 55 and urge the staples 58 from the staple pockets 55 towards the tissue facing surface 48 of the anvil plate 42 of the anvil assembly 40.

For a detailed description of the structure and function of exemplary surgical stapling apparatus, reference may be made to U.S. Pat. Nos. 6,330,965, 6,241,139, and 7,819,896, the entire contents of each of which are incorporated herein by reference. It should be appreciated that principles of the present disclosure are equally applicable to surgical stapling apparatus having other configurations such as, for example, the types described in U.S. Pat. Nos. 7,128,253, 7,334,717, and 5,964,394, the entire contents of each of which are incorporated herein by reference. Accordingly, it should be understood that a variety of surgical stapling apparatus may be utilized with the surgical buttress retention systems of the present disclosure. For example, laparoscopic or open staplers, such as, for example, GIA™, Endo GIA™, TA™, and Endo TA™ staplers and/or linear and radial reloads with, for example, Tri-Staple™ technology, available through Medtronic (North Haven, Conn.) may be utilized with the surgical buttress retention systems of the present disclosure.

With continued reference to FIG. 3, the anvil assembly 40 further includes proximal anvil guide slots 43, distal anvil guide slots 45, and an anvil plug 47. The proximal anvil guide slots 43 and the distal anvil guide slots 45 are recessed in the outer surface 46 of the anvil cover 44. The proximal anvil guide slots 43 are disposed in opposed sides of the anvil cover 44, and are mirror images of each other. The proximal anvil guide slots 43 have a generally U-shaped configuration in that each of the proximal anvil guide slots 43 include a central segment 43b extending longitudinally along the anvil cover 44 and a first or proximal leg segment 43a and a second or distal leg segment 43c each extending at an angle with respect to the central segment 43b to side edges 44a, 44b of the anvil cover 44. The first and second leg segments 43a, 43c may extend at the same or different angles with respect to the central segment 43b. In embodiments, the first leg segment 43a is disposed at about a 90° angle with respect to the central segment 43b and the second leg segment 43c is disposed at about a 135° angle with respect to the central segment 43b. In some embodiments, as shown in FIG. 2, the first leg segment 43a is disposed at about a 90° angle with respect to the central segment 43b and the second leg segment 43c' is disposed at about a 90° angle with respect to the central segment 43b. The anvil plate 42 may include recesses 42c defined in side edges 42a, 42b thereof that are aligned with the first and second leg segments 43a, 43b of the proximal anvil guide slots 43.

The distal anvil guide slots 45 are disposed in opposed sides of the anvil cover 44 in longitudinally spaced relation relative to the proximal anvil guide slots 43, and are also mirror images of each other. The distal anvil guide slots 45 have a generally L-shaped configuration in that each of the distal anvil guide slots 45 have first and second leg segments 45a, 45b that are disposed at an angle with respect to each other. In embodiments, the first leg segment 45a is disposed at about a 135° angle with respect to the second leg segment 45b which extends longitudinally along the anvil cover 44 to a distal end 44c thereof. In some embodiments, as shown in FIG. 2, the first leg segment 45a' is disposed at about a 90° angle with respect to the second leg segment 45b which extends longitudinally along the anvil cover 44 to the distal end 44c thereof.

The anvil plug 47 has a cylindrical body 47a that is configured to releasably engage the distal end 44c of the anvil cover 44. In embodiments, the anvil plug 47 is press fit into an anvil recess 49 defined in the distal end 44c of the anvil cover 44. The anvil plug 47 may include an aperture 47b defined therethrough.

With continued reference to FIG. 3, the staple cartridge assembly 50 further includes proximal cartridge guide slots 73, distal cartridge guide slots 75, and a cartridge plug 77. The proximal cartridge guide slots 73 are recessed in side surfaces 52a, 52b of the cartridge carrier 52, and the distal cartridge guide slots 77 are recessed in an outer surface 54a of the staple cartridge 54. While only one of the proximal and distal cartridge guide slots 73, 75 are shown in FIG. 3, it should be understood that the other of the proximal and distal cartridge guide slots 73, 75 are substantially identical to ones shown and are disposed in oppose sides of the respective cartridge carrier 52 and staple cartridge 54 as mirror images of the ones shown.

The proximal cartridge guide slots 73 have a generally U-shaped configuration in that each of the proximal cartridge guide slots 73 include a central segment 73b extending longitudinally along the cartridge carrier 52 and a first or proximal leg segment 73a and a second or distal leg segment 73c each extending at an angle with respect to the central segment 73b. The first and second leg segments 73a, 73c may extend at the same or different angles with respect to the central segment 73b. In embodiments, the first leg segment 73a is disposed at about a 90° angle with respect to the central segment 73b and the second leg segment 73c is disposed at about a 135° angle with respect to the central segment 73b. In some embodiments, as shown in FIG. 2, the first leg segment 73a is disposed at about a 90° angle with respect to the central segment 73b and the second leg segment 73c' is disposed at about a 90° angle with respect to the central segment 73b.

The distal cartridge guide slots 75 have a generally L-shaped configuration in that each of the distal cartridge guide slots 75 have first and second leg segments 75a, 75b that are disposed at an angle with respect to each other. In embodiments, the first leg segment 75a is disposed at about a 135° angle with respect to the second leg segment 75b which extends transversely across a distal portion 54b of the staple cartridge 54. In some embodiments, as shown in FIG. 2, the first leg segment 75a' is disposed at about a 90° angle with respect to the second leg segment 75b which extends transversely across the distal portion 54b of the staple cartridge 54.

The cartridge plug 77 has a cylindrical body 77a that is configured to releasably engage a cartridge recess 51 defined in the distal portion 54b of the staple cartridge 54. In embodiments, the cartridge plug 77 is press fit into the cartridge recess 51 of the staple cartridge 54. The cartridge plug 77 may include an aperture 77b defined therethrough.

Figure 4:
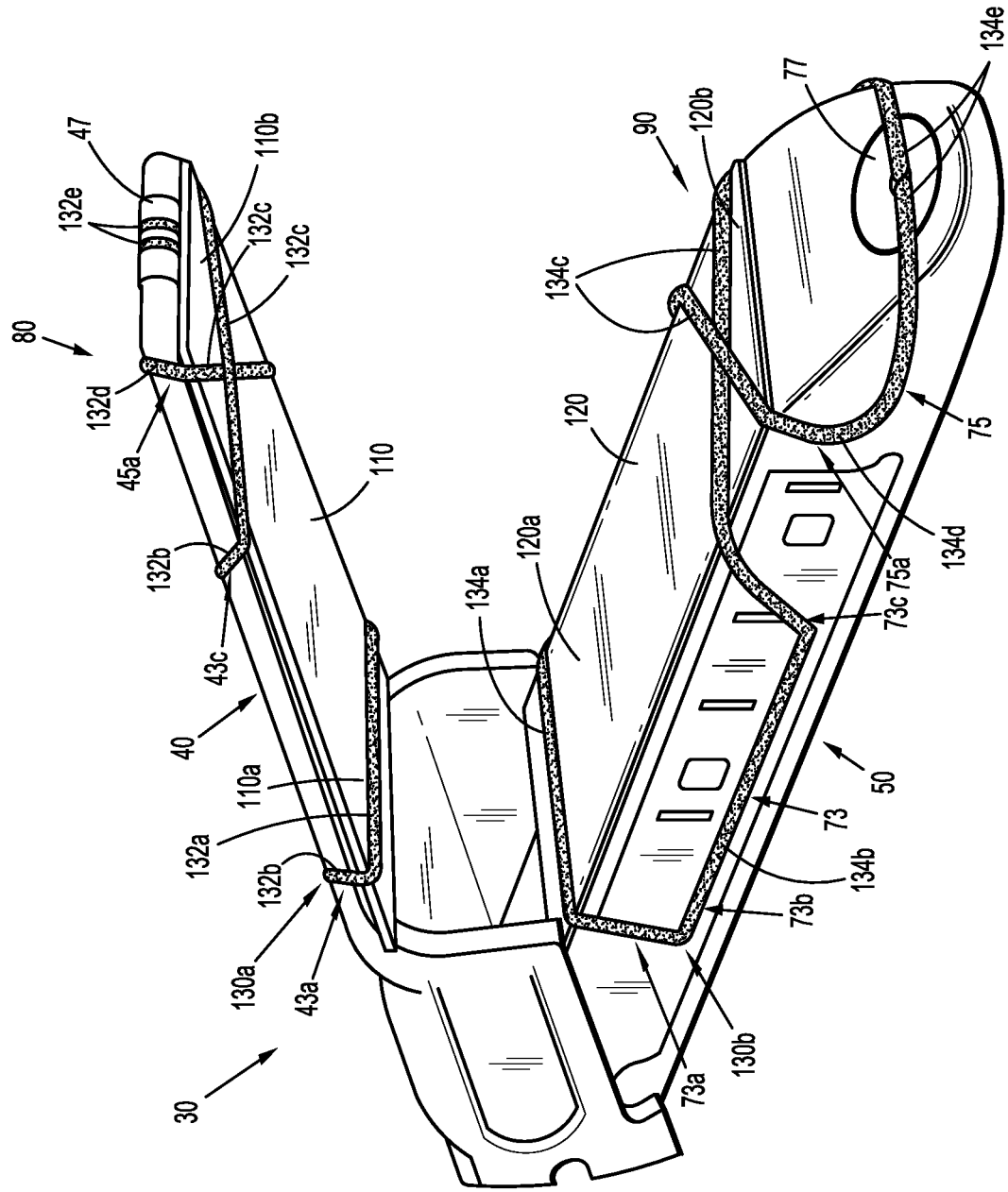
FIG. 4 is an end, perspective view of the jaw assembly of FIG. 3, including surgical buttresses releasably secured to the anvil and staple cartridge assemblies via retention members in accordance with an embodiment of the present disclosure.

With reference now to FIG. 4, surgical buttresses 110, 120 (also referred to herein as anvil buttress 110 and cartridge buttress 120) are releasably attached to the respective anvil and staple cartridge assemblies 40, 50 of the jaw assembly 30 of the surgical stapler 1 (FIG. 1) by retention members 130a, 130b (also referred to herein as anvil retention member 130a and cartridge retention member 130b). The surgical buttresses 110, 120 are fabricated from biocompatible materials which are bioabsorbable or non-absorbable, natural or synthetic materials. It should be understood that any combination of natural, synthetic, bioabsorbable, and/or non-bioabsorbable materials may be used to form the surgical buttresses 110, 120. The surgical buttresses 110, 120 may be formed from the same material or different materials.

The surgical buttresses 110, 120 may be porous, non-porous, or combinations thereof. Suitable porous structures include, for example, fibrous structures (e.g., knitted structures, woven structures, and non-woven structures) and/or foams (e.g., open or closed cell foams). Suitable non-porous structures include, for example, films. The surgical buttresses 110, 120 described herein may be a single porous or non-porous layer, or include a plurality of layers including any combination of porous and non-porous layers. For example, a surgical buttress may include multiple porous and non-porous layers that are stacked in an alternating manner. In another example, a surgical buttress may be formed in a "sandwich-like" manner wherein the outer layers of the surgical buttress are porous and the inner layer(s) are non-porous, or vice versa. The surgical buttresses 110, 120 may have the same or a different structure of layer(s).

Porous layer(s) in a surgical buttress may enhance the ability of the surgical buttress to absorb fluid, reduce bleeding, and seal a wound. Also, the porous layer(s) may allow for tissue ingrowth to fix the surgical buttress in place. Non-porous layer(s) in a surgical buttress may enhance the ability of the surgical buttress to resist tears and perforations during the manufacturing, shipping, handling, and stapling processes. Also, non-porous layer(s) may retard or prevent tissue ingrowth from surrounding tissues thereby acting as an adhesion barrier and preventing the formation of unwanted scar tissue.

The retention members 130a, 130b are fabricated from biocompatible materials which are any combination of natural, synthetic, bioabsorbable, and/or non-bioabsorbable materials. Each of the retention members 130a, 130b is a single continuous elongated structure, and may be in the form of a suture, thread, filament, etc.

With continued reference to FIG. 4, in conjunction with FIG. 3, the anvil buttress 110 is releasably secured to the anvil assembly 40 via an anvil buttress retention system 80 including the anvil retention member 130a in cooperation with the proximal and distal anvil guide slots 43, 45 (FIG. 3) and the anvil plug 47 of the anvil assembly 40. With the anvil buttress 110 positioned on the tissue facing surface 48 of the anvil plate 42, a central or first portion 132a of the anvil retention member 130a is positioned across a proximal portion 110a of the anvil buttress 110 and aligned with the first leg segments 43a of the proximal anvil guide slots 43 such that second portions 132b of the anvil retention member 130a are positioned within the proximal anvil guide slots 43. In embodiments in which the first leg segments 43a of the proximal anvil guide slots 43 are disposed at about a 90° angle with respect to the central segment 43b, the first portion 132a of the anvil retention member 130a will be retained transversely across the proximal portion 110a of the anvil buttress 110.

Third portions 132c of the anvil retention member 130a extend from the proximal anvil guide slots 43 and cross each other over a distal portion 110b of the anvil buttress 110, and fourth portions 132d of the anvil retention member 130a are positioned within the distal anvil guide slots 45. In embodiments in which the second leg segments 43c of the proximal anvil guide slots 43 and the first leg segments 45a of the distal anvil guide slots 45 are disposed at about 135° angles, as described above, the anvil retention member 130a follows an aligned path for the cross over transition over the distal portion 110b of the anvil buttress 110. Fifth or end portions 132e of the anvil retention member 130a are coupled to the anvil plug 47 to retain the anvil retention member 130a on the anvil assembly 40 and over the anvil buttress 110.

The fifth portions 132e of the anvil retention member 130a may be wound around the anvil plug 47 to tension the anvil retention member 130a on the anvil assembly 40. The fifth portions 132e may be wound around the anvil plug 47 prior to positioning the anvil plug 47 within the anvil recess 49 or while the anvil plug 47 is positioned within the anvil recess 49 (e.g., by rotating the anvil plug 47 relative to the anvil cover 44). In embodiments, the fifth portions 132e are passed into the aperture 47b of the anvil plug 47 and retained therein such that the anvil plug 47 may be rotated relative to the anvil cover 44 to tension the anvil retention member 130a about the anvil buttress 110 and the anvil assembly 40.

The configuration of the proximal and distal anvil guide slots 43, 45 as well as the positioning of the anvil retention member 130a therethrough minimizes and/or prevents pinch points along the anvil retention member 130a to allow for smooth insertion, tensioning, and deployment of the anvil retention member 130a. Moreover, the depth of the proximal and distal anvil guide slots 43, 45 may be configured to ensure that the anvil retention member 130a is flush with the outer surfaces of the anvil assembly 40 to reduce and/or eliminate the occurrence of the anvil retention member 130a moving out of alignment with the proximal and/or distal anvil guide slots 43, 45 during, for example, translation of the anvil retention member 130a relative to the anvil assembly 40 during tensioning thereof and/or during insertion into tissue when outside forces may act upon the jaw assembly 30.

As also shown in FIG. 4, in conjunction with FIG. 3, the cartridge buttress 120 is releasably secured to the staple cartridge assembly 50 via a cartridge buttress retention system 90 including the cartridge retention member 130b in cooperation with the proximal and distal cartridge guide slots 73, 75 (FIG. 3), and the cartridge plug 77 of the staple cartridge assembly 50. With the cartridge buttress 120 positioned on the tissue facing surface 56 of the staple cartridge 54, a central or first portion 134a of the cartridge retention member 130b is positioned across a proximal portion 120a of the cartridge buttress 120 and aligned with the first leg segments 73a of the proximal cartridge guide slots 73 such that second portions 134b of the cartridge retention member 130b are positioned within the proximal cartridge guide slots 73. In embodiments in which the first leg segments 73a of the proximal cartridge guide slots 73 are disposed at about a 90° angle with respect to the central segment 73b, the first portion 134a of the cartridge retention member 130b will be retained transversely across the proximal portion 120b of the cartridge buttress 120.

Third portions 134c of the cartridge retention member 130b extend from the proximal cartridge guide slots 73 and cross each other over a distal portion 120b of the cartridge buttress 120, and fourth portions 134d of the cartridge retention member 130b are positioned within the distal cartridge guide slots 75. In embodiments in which the second leg segments 73c of the proximal cartridge guide slots 73 and the first leg segments 75a of the distal cartridge guide slots 75 are disposed at about 135° angles, as described above, the buttress retention member 130b follows an aligned path for the cross over transition over the distal portion 120b of the cartridge buttress 120. Fifth or end portions 134e of the cartridge retention member 130b are coupled to the cartridge plug 77 to retain the cartridge retention member 130b on the staple cartridge assembly 50 and over the cartridge buttress 120.

The fifth portions 134e of the cartridge retention member 130b may be wound around the cartridge plug 77 to tension the cartridge retention member 130b on the staple cartridge assembly 50. The fifth portions 134e may be wound around the cartridge plug 77 prior to positioning the cartridge plug 77 within the cartridge recess 51 or while the cartridge plug 77 is positioned within the cartridge recess 51 (e.g., by rotating the cartridge plug 77 relative to the staple cartridge 54). In embodiments, the fifth portions 134e are passed through the aperture 77b of the cartridge plug 77 and retained therein such that the cartridge plug 77 may be rotated relative to the staple cartridge 54 to tension the cartridge retention member 130b about the cartridge buttress 120 and the staple cartridge assembly 50.

The configuration of the proximal and distal cartridge guide slots 73, 75 as well as the positioning of the cartridge retention member 130b therethrough minimizes and/or prevents pinch points along the cartridge retention member 130b to allow for smooth insertion, tensioning, and deployment of the cartridge retention member 130b. Moreover, the depth of the proximal and distal cartridge guide slots 73, 75 may be configured to ensure that the cartridge retention member 130b is flush with the outer surfaces of the staple cartridge assembly 50 to reduce and/or eliminate the occurrence of the cartridge retention member 130b moving out of alignment with the proximal and/or distal cartridge guide slots 73, 75 during, for example, translation of the cartridge retention member 130b relative to the staple cartridge assembly 50 during tensioning thereof and/or during insertion into tissue when outside forces may act upon the jaw assembly 30.

In a method of loading the anvil and cartridge buttresses 110, 120 onto the anvil and staple cartridge assemblies 40, 50, the anvil and cartridge buttresses 110, 120 are positioned over the respective tissue facing surfaces 48, 56 of the anvil and staple cartridge assemblies 40, 50, and then the anvil and cartridge retention members 130a, 130b are engaged with the respective proximal anvil and cartridge guide slots, 43, 73, the distal anvil and cartridge guide slots, 45, 75, and the anvil and cartridge plug members 47, 77, as described above. The anvil and cartridge retention members 130a, 130b are tensionable via the anvil and cartridge plug members 47, 77, as also described above. Alternatively, the anvil and buttress retention systems 80, 90 may be assembled, the anvil and cartridge buttresses 110, 120 may be slid under the respective anvil and cartridge retention members 130a, 130b, and then the anvil and cartridge retention members 130a, 130b may be tensioned over the anvil and cartridge buttresses 110, 120. The jaw assembly 30 is thus loaded and ready for use, as shown in FIG. 4.

In operation, with the anvil and cartridge buttress 110, 120 loaded onto the anvil and staple cartridge assemblies 40, 50, as described above, the surgical stapler 1 is used in accordance with methods known by those skilled in the art. Once the anvil and staple cartridge assemblies 40, 50 are clamped onto tissue (e.g., moved from the open position shown, for example, in FIG. 4, to the closed position, shown, for example, in FIG. 2), the surgical stapler 1 is fired. In firing the surgical stapler 1, the drive bar 64 is advanced distally through the jaw assembly 30 urging the staple pushers 60 upwardly which, in turn, drive the staples 58 out of the staple pockets 55 and through the anvil and cartridge buttresses 110, 120 as well as the captured tissue, thereby stapling the anvil and cartridge buttresses 110, 120 to the tissue.

During firing, the knife blade 62 of the drive bar 64 travels distally while substantially simultaneously cutting and dividing the tissue and the anvil and cartridge buttresses 110, 120 disposed between the rows of now formed staples 58. As the first portions 132a, 134a of the anvil and cartridge retention members 130a, 130b extend across the respective proximal portions 110a, 120a of the anvil and cartridge buttresses 110, 120 above the respective central longitudinal slots 41, 57 of the anvil and staple cartridge assemblies 40, 50, the knife blade 62 also cuts through the first portions 132a, 134a of the anvil and cartridge retention members 130a, 130b. The proximal cut of the first portions 132a, 134a of the anvil and cartridge retention members 130a, 130b releases the tension on the anvil and cartridge retention members 130a, 130b and loosens the anvil and cartridge retention members 130a, 130b, freeing the anvil and cartridge buttresses 110, 120 from the anvil and staple cartridge assemblies 40, 50.

When firing is complete, after a partial or full firing stroke, and the anvil and staple cartridge assemblies 40, 50 are unclamped, the anvil and cartridge buttresses 110, 120, which are now stapled to the tissue, pull away from the anvil and staple cartridge assemblies 40, 50, while the anvil and buttress retention members 130a, 130b are retained on the anvil and staple cartridge assemblies 40, 50 (via the anvil and cartridge plugs 47, 77) and removed from the surgical site with the removal of the jaw assembly 30 therefrom. Accordingly, the anvil and cartridge buttresses 110, 120 are released from the surgical stapler 1 after a partial or full firing stroke by requiring only a single proximal cut of the anvil and cartridge retention members 130a, 130b. Further, as cutting of the tissue follows staple formation, the proximal cut of the anvil and cartridge retention members 130a, 130b ensures that any tissue that is cut is also stapled and reinforced with the anvil and cartridge buttresses 110, 120.

With reference now to FIGS. 5 and 6, a jaw assembly 30' in accordance with another embodiment of the present disclosure is shown. The jaw assembly 30' has an anvil assembly 40' including an anvil plate 42 and an anvil cover 44', and a staple cartridge assembly 50' including a carrier cartridge 52' and a staple cartridge 54'. The jaw assembly 30' is substantially similar to the jaw assembly 30 and will be described in detail herein to the extent necessary to describe the differences in construction and operation thereof.

The anvil assembly 40' includes a proximal anvil guide assembly 140, a distal anvil guide assembly 144, and an anvil plug 47. The proximal guide assembly 140 includes proximal anvil guide cleats or bumpers 142a disposed on opposed sides of the anvil cover 44'. The proximal anvil guide cleats 142a protrude or extend from an outer surface 46' of the anvil cover 44' and have a rounded shape. The proximal guide assembly 140 further includes distal anvil guide cleats or bumpers 142b disposed on opposed sides of the anvil cover 44' in longitudinally spaced and aligned relation relative to the proximal anvil guide cleats 142a. The distal anvil guide cleats 142b also protrude or extend from an outer surface 46' of the anvil cover 44' and have a rounded shape. The proximal and distal anvil guide cleats 142a, 142b may be formed from a soft and/or flexible material (e.g., a polymeric material) to minimize trauma to tissue during insertion of the jaw assembly 30' into a surgical site.

The distal anvil guide assembly 144 includes anvil guide shoulders 146 extending from the outer surface 46' of the anvil cover 44. The anvil guide shoulders 146 are disposed on opposed sides of the anvil cover 44' and are images of each other. The anvil guide shoulders 146 have a generally L-shaped or C-shaped configuration including soft, rounded edges. The anvil guide shoulders 146 may also be formed from a soft and/or flexible material.

The staple cartridge assembly 50' includes a proximal cartridge guide assembly 150, a distal cartridge guide assembly 154, and a cartridge plug 77. The proximal cartridge guide assembly 150 includes proximal and distal cartridge guide cleats or bumpers 152a, 152b disposed on opposed sides of the cartridge carrier 52', and the distal cartridge guide assembly 154 includes cartridge guide shoulders 156 disposed on opposed sides of the staple cartridge 54'. While only one of the proximal and distal cartridge guide cleats 152a, 152b, and cartridge guide shoulders 156 are shown, it should be understood that the other of the respective proximal and distal cartridge guide cleats 152a, 152b, and cartridge guide shoulders 156, are substantially identical to the ones shown and are positioned on the opposing side of the cartridge carrier 52' and staple cartridge 54' as mirror images of each other.

The proximal and distal cartridge guide cleats 152a, 152b protrude or extend from side surfaces 52a', 52b' of the cartridge carrier 52', and each has a rounded shape. The distal cartridge guide cleats 152b are longitudinally spaced from, and aligned with, the proximal cartridge guide cleats 152a. The cartridge guide shoulders 156 extend from opposed sides of a distal portion 54b' of the staple cartridge 54', and each has a generally L-shaped or C-shaped configuration including soft, rounded edges. The proximal and distal cartridge guide cleats 152a, 152b, and/or the cartridge guide shoulders 156 may be formed from a soft and/or flexible material (e.g., a polymeric material) to minimize trauma to tissue during insertion of the jaw assembly 30' into a surgical site.

With continued reference to FIGS. 5 and 6, an anvil buttress 110 is releasably secured to the anvil assembly 40' via an anvil buttress retention system 180 including an anvil retention member 130a in cooperation with the proximal and distal anvil guide assemblies 140, 142, and the anvil plug 47 of the anvil assembly 40'. With the anvil buttress 110 positioned on the tissue facing surface 48 (FIG. 3) of the anvil plate 42, a central or first portion 132a of the anvil retention member 130a is positioned across a proximal portion 110a of the anvil buttress 110 and aligned with proximally facing sides of the proximal anvil guide cleats 142a such that second portions 132b of the anvil retention member 130a extend around the proximal anvil guide cleats 142a, longitudinally across the outer surface 46' of the anvil cover 44', and around the distal anvil guide cleats 142b.

Third portions 132c of the anvil retention member 130a extend from distally facing sides of the distal anvil guide cleats 142b and cross each other over a distal portion 110b of the anvil buttress 110. Fourth portions 132d of the anvil retention member 130a are positioned around the anvil guide shoulders 146, and fifth or end portions 132e of the anvil retention member 130a are coupled to the anvil plug 47 to retain the anvil retention member 130a on the anvil assembly 40' and over the anvil buttress 110, as described above.

The configuration of the proximal and distal anvil guide cleats 142a, 142b and the anvil guide shoulders 146 (e.g., the rounded sides and/or material selection), as well as the positioning of the anvil retention member 130a therearound minimizes and/or prevents pinch points along the anvil retention member 130a to allow for smooth insertion, tensioning, and deployment of the anvil retention member 130a.

As also shown in FIGS. 5 and 6, a cartridge buttress 120 is releasably secured to the staple cartridge assembly 50' via a cartridge buttress retention system 190 including a cartridge retention member 130b in cooperation with the proximal and distal cartridge guide assemblies 150, 152, and the cartridge plug 77 of the staple cartridge assembly 50'. With the cartridge buttress 120 positioned on the tissue facing surface 56 (FIG. 3) of the staple cartridge 54', a central or first portion 134a of the cartridge retention member 130b is positioned across a proximal portion 120a of the cartridge buttress 120 and aligned with proximally facing sides of the proximal cartridge guide cleats 152a such that second portions 134b of the cartridge retention member 130b extend around the proximal cartridge guide cleats 152a, longitudinally along the cartridge carrier 52', and around the distal cartridge guide cleats 152b.

Third portions 134c of the cartridge retention member 130b extend from distally facing sides of the distal anvil guide cleats 152b and cross each other over a distal portion 120b of the cartridge buttress 120. Fourth portions 134d of the cartridge retention member 130b are positioned around the cartridge guide shoulders 156, and fifth or end portions 134e of the cartridge retention member 130b are coupled to the cartridge plug 77 to retain the cartridge retention member 130b on the staple cartridge assembly 50' and over the cartridge buttress 120, as described above.

The configuration of the proximal and distal cartridge guide cleats 152a, 152b and the cartridge guide shoulders 156 (e.g., the rounded sides and/or material selection), as well as the positioning of the cartridge retention member 130b therearound minimizes and/or prevents pinch points along the cartridge retention member 130b to allow for smooth insertion, tensioning, and deployment of the cartridge retention member 130b.

A surgical stapler 1 including the jaw assembly 30' having anvil and cartridge buttresses 110, 120 loaded onto the anvil and staple cartridge assemblies 40', 50' via the anvil and cartridge buttress retention systems 180, 190, as described above, is operated in the same manner as described above with respect to the surgical stapler 1 including the jaw assembly 30 having anvil and cartridge buttresses 110, 120 loaded onto the anvil and staple cartridge assemblies 40, 50 via the anvil and cartridge buttress retention systems 80, 90.

It should be understood that the anvil buttress retention systems 80, 180, the cartridge buttress retention systems 90, 190, and/or components thereof, may be used together. For example, the proximal anvil guide slots 43 of the anvil buttress retention system 80 may be used with the proximal and distal anvil guide cleats 142a, 142b of the anvil buttress retention system 180, and/or the distal anvil guide slots 45 of the anvil buttress retention system 80 may be used with the anvil guide shoulders 146 of the anvil buttress retention system 180. Similarly, the proximal cartridge guide slots 73 of the cartridge buttress retention system 90 may be used with the proximal and distal cartridge guide cleats 152a, 152b of the cartridge buttress retention system 190, and/or the distal cartridge guide slots 75 of the cartridge buttress retention system 90 may be used with the cartridge guide shoulders 156 of the cartridge buttress retention system 190. As another example, the proximal and distal anvil guide cleats 142a, 142b of the anvil buttress retention system 180 may be used with the central segments 43b of the proximal anvil guide slots 43 of the anvil buttress retention system 80, and/or the anvil guide shoulders 146 of the anvil buttress retention system 180 may be used with the second leg segments 45b of the distal anvil guide slots 45 of the anvil buttress retention system 80. Similarly, the proximal and distal cartridge guide cleats 152a, 152b of the cartridge buttress retention system 190 may be used with the central segments 73b of the proximal cartridge guide slots 73 of the cartridge buttress retention system 90, and/or the cartridge guide shoulders 156 of the cartridge buttress retention system 190 may be used with the second leg segments 75b of the distal cartridge guide slots 75 of the cartridge buttress retention system 90. A variety of combinations of the components of the anvil and cartridge buttress retention systems are envisioned, provided such result in smooth insertion, tensioning, and deployment of the retention members, as described above.

It should be further understood that while the surgical stapler 1 is shown including both the anvil and cartridge buttresses 110, 120, the surgical stapler 1 may include only the anvil buttress 110 or the cartridge buttress 120 depending on, for example, the surgical application and/or desired placement of the buttress material relative to tissue as should be understood by those skilled in the art. The anvil buttress 110 and/or the cartridge buttress 120 may be pre-loaded (e.g., by the manufacturer) onto the anvil assembly 40, 40' and/or staple cartridge assembly 50, 50' of the jaw assembly 30, 30'. Additional or replacement anvil buttresses 110 and/or cartridge buttresses 120 may be secured to the respective anvil assembly 40, 40' and/or staple cartridge assembly 50, 50' as needed or desired.

The surgical buttresses and anvil buttress retention systems described herein may also be configured for use with other surgical apparatus, such as electromechanical surgical devices as described, for example, in U.S. Patent Appl. Pub. Nos. 2015/0157320 and 2015/0157321, the entire contents of each of which are incorporated herein by reference.

Persons skilled in the art will understand that the systems, devices, and methods specifically described herein and illustrated in the accompanying figures are non-limiting exemplary embodiments, and that the description, disclosure, and figures should be construed merely exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another exemplary embodiment without departing from the scope of the present disclosure, and that such modifications and variations are also intended to be included within the scope of the present disclosure. Accordingly, the subject matter of the present disclosure is not to be limited by what has been particularly shown and described.

What is claimed is:

1. An anvil buttress retention system comprising:
   an anvil assembly including a tissue facing surface;
   an anvil plug rotatably coupled to the anvil assembly;
   a surgical buttress disposed on the tissue facing surface of the anvil assembly; and
   a retention member coupled to the anvil plug and positioned on the anvil assembly and the surgical buttress, wherein rotation of the anvil plug tensions the retention member about the anvil assembly and the surgical buttress to releasably secure the surgical buttress to the anvil assembly.

2. The anvil buttress retention system according to claim 1, wherein the anvil plug is releasably engaged with the anvil assembly.

3. The anvil buttress retention system according to claim 1, wherein the anvil plug is disposed within an aperture defined in the anvil assembly.

4. The anvil buttress retention system according to claim 3, wherein the anvil plug is press fit into the aperture.

5. The anvil buttress retention system according to claim 1, wherein the anvil plug is coupled to a distal end of the anvil assembly.

6. The anvil buttress retention system according to claim 1, wherein the anvil plug includes a cylindrical body.

7. The anvil buttress retention system according to claim 1, wherein the anvil plug includes an aperture defined therethrough, and end portions of the retention member extend through the aperture and are retained therein.

8. The anvil buttress retention system according to claim 1, wherein the anvil assembly further includes anvil guide slots recessed in an outer surface of the anvil assembly, and portions of the retention member are positioned within the anvil guide slots.

9. The anvil buttress retention system according to claim 1, wherein the anvil assembly further includes anvil guide cleats extending outwardly from an outer surface of the anvil assembly, and portions of the retention member are positioned around the anvil guide cleats.

10. The anvil buttress retention system according to claim 1, where the anvil assembly further includes anvil guide shoulders extending outwardly from an outer surface of the anvil assembly, and portions of the retention member are positioned around the anvil guide shoulders.

11. A cartridge buttress retention system comprising:
    a staple cartridge assembly including a tissue facing surface;
    a cartridge plug rotatably coupled to the staple cartridge assembly;
    a surgical buttress disposed on the tissue facing surface of the staple cartridge assembly; and
    a retention member coupled to the cartridge plug and positioned on the staple cartridge assembly and the surgical buttress, wherein rotation of the cartridge plug tensions the retention member about the staple cartridge assembly and the surgical buttress to releasably secure the surgical buttress to the staple cartridge assembly.

12. The cartridge buttress retention system according to claim 11, wherein the cartridge plug is releasably engaged with the staple cartridge assembly.

13. The cartridge buttress retention system according to claim 11, wherein the cartridge plug is disposed within an aperture defined in the staple cartridge assembly.

14. The cartridge buttress retention system according to claim 13, wherein the cartridge plug is press fit into the aperture.

15. The cartridge buttress retention system according to claim 11, wherein the cartridge plug is coupled to a distal end portion of the staple cartridge assembly.

16. The cartridge buttress retention system according to claim 11, wherein the cartridge plug includes a cylindrical body.

17. The cartridge buttress retention system according to claim 11, wherein the cartridge plug includes an aperture defined therethrough, and end portions of the retention member extend through the aperture and are retained therein.

18. The cartridge buttress retention system according to claim 11, wherein the staple cartridge assembly further includes cartridge guide slots recessed in side surfaces of the staple cartridge assembly, and portions of the retention member are positioned within the cartridge guide slots.

19. The cartridge buttress retention system according to claim 11, wherein the staple cartridge assembly further includes cartridge guide cleats extending outwardly from side surfaces of the staple cartridge assembly, and portions of the retention member are positioned around the cartridge guide cleats.

20. The cartridge buttress retention system according to claim 11, where the staple cartridge assembly further includes cartridge guide shoulders extending outwardly from side surfaces of the staple cartridge assembly, and portions of the retention member are positioned around the cartridge guide shoulders.

\* \* \* \* \*